United States Patent [19]

Tatsuno et al.

[11] Patent Number: 5,147,605
[45] Date of Patent: Sep. 15, 1992

[54] METHOD FOR THE STERILIZATION OF ULTRAPURE WATER LINE

[75] Inventors: Toshio Tatsuno; Mitsuo Miyamoto, both of Osaka; Yoshiharu Ohta; Koichi Sawada, both of Tokyo, all of Japan

[73] Assignee: Morita Kagaku Kogyo Co., Ltd., Osaka, Japan

[21] Appl. No.: 487,937

[22] Filed: Mar. 5, 1990

[30] Foreign Application Priority Data

Mar. 6, 1989 [JP] Japan .................................. 1-52153

[51] Int. Cl.$^5$ .............................................. A01N 59/10
[52] U.S. Cl. ........................................ 422/37; 422/28; 422/292
[58] Field of Search ............................ 422/28, 37, 292; 210/640; 55/158

[56] References Cited

U.S. PATENT DOCUMENTS 4,879,041  11/1989  Kurokawa et al. ..................... 55/158
4,936,955  6/1990  Dobson et al. ....................... 202/154

FOREIGN PATENT DOCUMENTS 1584845  3/1977  United Kingdom.

Primary Examiner—James C. Housel
Assistant Examiner—Thomas E. Daley
Attorney, Agent, or Firm—Larson and Taylor

[57] ABSTRACT

Periodical sterilization is usually needed in the ultrapure water line provided in an ultrapure water-producing system or plant to kill some occasionally occurring viable cells of microorganisms in the ultrapure water as produced or being produced and thereby keep the ultrapure water under germ-free conditions. Now, it is discovered that an aqueous solution containing 1 to 100 ppm of hydrofluoric acid is effective to sterilize the ultrapure water line and is advantageous over the conventional sterilization agents such as aqueous hydrogen peroxide and sodium hypochlorite which were employed normally for the sterilization of the ultrapure water line.

5 Claims, 1 Drawing Sheet

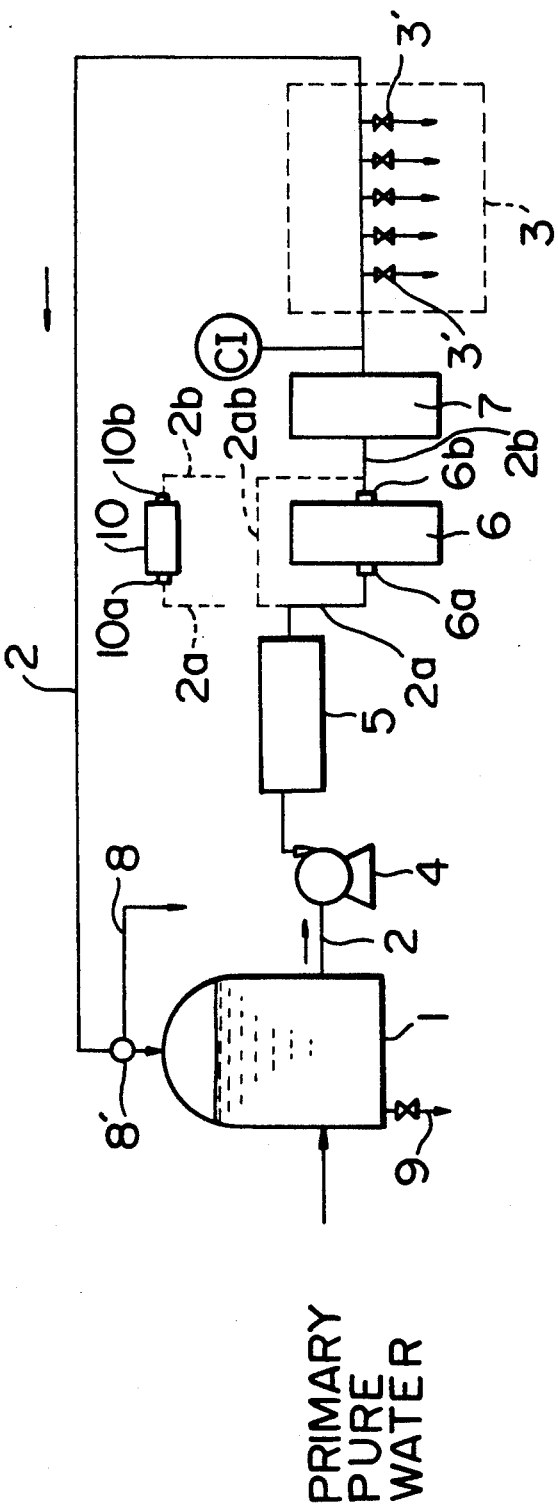

METHOD FOR THE STERILIZATION OF ULTRAPURE WATER LINE

SUMMARY OF THE INVENTION

The present invention relates to a method for the sterilization of an ultrapure water line provided in an ultrapure water-producing system or plant, and ultrapure water produced is used in the semiconductor industry or the like.

BACKGROUND OF THE INVENTION

To produce ultrapure water for use in the semiconductor industry, it is necessary not only to remove from the raw water various ions, fine solid particles and total organic carbon (TOC) to their ultimate minimum levels but also to get rid of cells of microorganisms (e.g., bacteria) from the water, because the inclusion of such microbial cells will adversely affect the yield of semiconductor products. In addition, it is also necessary to always maintain, under germ-free conditions, the ultrapure water line provided in the plant or system which is used for the production of ultrapure water. The ultrapure water line includes a system or a series of devices which is connected to a primary pure water-containing tank and is to achieve the ultimate purification of primary pure water into ultrapure water and comprises various treatment equipments, conduits, pump, valves, an ultrapure water-distributing equipment, and others incorporated in said system. As a means for removing the microbial cells from pure water, a reverse osmosis equipment, ultrafiltration equipment, microfilter or the like is used. To maintain the ultrapure water line under the germ-free conditions, an ultraviolet-radiating sterilizer is normally incorporated in the ultrapure water line to prevent the growth of viable cells (for example, bacteria).

However, such cell-removing equipment as provided in the ultrapure water line does not always perfectly operate. During long-term running of the plant, therefore, viable cells sometimes partly leak from the cell-removing equipment or intrude into the line externally through an air-exposed portion and/or a sealing packings in the line. Those viable cells then grow within the line and hence deteriorate the quality of ultrapure water as produced, thereby in some instances causing deleterious effects to the production yield of satisfactory semiconductor products.

It is therefore the common practice that an ultra-pure water line is periodically subjected to the sterilization to kill the viable cells.

Various methods have been proposed for the sterilization of the ultrapure water line. The general practice is to sterilize the line by the introduction of a bactericide thereinto. Usually, an ultrapure water line is subjected to such a sterilization treatment which comprises passing through the line an aqueous water containing 1-3 wt. % of hydrogen peroxide (hereinafter abbreviated as "$H_2O_2$") or aqueous sodium hypochlorite (NaClO) for one hour [Haruhiko Oya: "Handbook of Film Utilization Technology", K. K. Saiwai Shobo].

According to such a conventional method for sterilization of an ultrapure water line, a large volume of an aqueous solution of $H_2O_2$ or NaClO is discharged as a waste effluent. Since this waste effluent cannot directly be discharged into the environment as such because of the problems of enviromental pollution, the waste effluent is once stored in a tank or pool, to which a reducing agent is added for neutralization of the waste liquor before it is discharged into the environment. Accordingly, substantial expense is incurred for the treatment of the waste effluent. Further, $H_2O_2$ and NaClO are strong oxidizing agents. Should these agents flow into an ion exchange unit or such a non-regenerable mixed bed ion exchange resin unit which is normally arranged in the ultrapure water line as a final means for removal of ions and is generally called a "polisher", the expensive ion exchange resin may be oxidatively decomposed and hence may become no longer operable. In addition, it is essential to subsequently flush the ultrapure water line with a great volume of pure water for a long time until complete elimination of $H_2O_2$ or NaClO is achieved.

DETAILED DESCRIPTION OF THE INVENTION

We, the present inventors, have proceeded with an investigation with a view toward developing a method for achieving sterilization of an ultrapure water line arranged in such an ultrapure water-producing system without the need for use of $H_2O_2$, NaClO, or the like. As a result, we have now found that the ultrapure water line can be effectively sterilized when an aqueous solution containing hydrofluoric acid (hereinafter abbreviated as "HF") at an extremely low concentration of 1-100 ppm is passed through the line. It has also been revealed that treatment of the aqueous HF solution with suitable ion exchange resins subsequent to the sterilization with HF permits effective removal of the fluoride anions from the aqueous HF solution remaining in the ultrapure water line as sterilized and can obviate the need for discharge of fluoride ion-containing aqueous effluent from the system.

In one aspect of the present invention, there is thus provided a method for the sterilization of an ultrapure water line provided in an ultrapure water-producing system, which comprises passing through the ultrapure water line an aqueous solution containing hydrofluoric acid at a concentration of 1-100 ppm., so that the ultrapure water line is sterilized.

As a specific embodiment for practising the present invention, there is also provided a method for the sterilization of an ultrapure water line provided in an ultrapure water-producing system, said ultrapure water line comprising an ion exchange resin unit as well as an inlet-side conduit section and an outlet-side conduit section as connected to an inlet and an outlet of the ion exchange resin unit, which method comprises:

(a) disconnecting from the ion exchange resin unit and connecting the inlet-side conduit section and the outlet-side conduit section directly to each other to form a bypass circuit and to permit bypassed feeding of water through said bypass circuit without passing the water through the ion exchange resin unit provided in the ultrapure water line;

(b) passing an aqueous solution containing hydrofluoric acid at a concentration of 1-100 ppm., through the ultrapure water line which has been rearranged by the direct connection of the inlet-side conduit section to the outlet-side conduit section to form the bypass circuit and permit the bypassed feeding of water without passing the water through the ion exchange resin unit, whereby the sterilization is effected in the so rearranged ultrapure water line; and (c) allowing the aqueous solution of hydrofluoric acid to remain within the ultrapure water line having been so rearranged to have the bypass circuit, until the sterilization has been completed in said ultrapure water line.

In another embodiment of the present invention, the present method may further comprise:

(d) disconnecting the inlet-side conduit section and outlet-side conduit section from each other after the completed sterilization, whereby the previous direct connection of the inlet-side conduit section to the outlet-side conduit section for permitting the bypassed feeding of water without the passage through the ion exchange resin unit is thus broken;

(e) immediately after the disconnection, connecting the inlet-side conduit section and the outlet-side conduit section respectively to an inlet and an outlet of a basic anion exchange resin unit as separately provided;

(f) circulating the aqueous hydrofluoric acid solution, which has been used for the sterilization of the line, through the basic anion exchange resin unit and through the ultrapure water line, to remove the fluoride ions from the aqueous hydrofluoric acid solution by the basic anion exhange resin; and (g) continuing the step (f) of circulation of the aqueous hydrofluoric acid solution until the remaining fluoride ions are removed from the circulating aqueous solution and the circulating aqueous solution becomes substantially free of the fluoride ions, but without discharging any fluoride ion-containing aqueous solution as an effluent from the ultrapure water-producing system. Subsequently to the completion of the above-mentioned circulation step (f) where the fluoride ion-containing aqueous solution has been continued to be circulated through the line for the removal of fluoride ions by the basic anion exchange resin unit, the method of the present invention may further comprise:

(h) replacing the basic anion exchange resin unit by a cartridge-type mixed bed ion exchange resin unit subsequently to the completion of the step (g) where the fluoride ion-containing aqueous solution has been continued to be circulated for the removal of fluoride ions by the basic anion exchange resin unit, with the cartridge-type mixed bed ion exchange resin unit as replaced being connected to said inlet-side conduit section and said outlet-side conduit section, respectively, and being thus incorporated in the ultrapure water line;

(i) circulating further the water remaining in the ultrapure water line, through the cartridge-type mixed bed ion exchange resin unit and through the ultrapure water line so that further removal of any residual ions and other impurities present in the water is achieved by the cartridge-type mixed bed ion exchange resin unit; and (j) continuing the circulation of the water through the cartridge-type mixed bed ion exchange resein unit and through the ultrapure water line until the electric resistivity of the circulating water reaches 17.5 MΩ.cm when measured at an outlet side of an ultrafiltration unit provided in the ultrapure water line and thus until the production of ultrapure water is ready for its re-starting. Thereafter, the production of ultrapure water can be resumed.

The present invention will now be described in detail with reference to FIG. 1 of the accompanying drawing.

FIG. 1 shows diagrammatically a flow chart of an ultrapure water line which is included in an ultrapure water-producing system. This ultrapure water line is suitable for use in the practice of the method according to the present invention, and this ultrapure water line comprises a pure water-containing tank 1; a circle line 2; the point 3 of use of ultrapure water; valves 3' of the ultrapure water-distributing pipes; a circle pump 4; an ultraviolet-radiating sterilizer 5; a cartridge-type ion exchange resin unit (the polisher) 6; an ultrafiltration membrane unit 7; a drain line 8 of the return section of the circle line 2; valves 8'; drain tube 9 of the tank 1, and an electric resistivity-measuring meter CI which are respectively provided in the ultrapure water line.

In general, the ultrapure water-producing system includes a primary pure water-producing system (line) (not shown) in which raw water is passed successively through certain pretreatment units, reverse osmosis unit, vacuum degasifier column, ion exchange column, and post-filter (each not shown) and which is to conduct the primary purification of raw water. The primary pure water coming from the primary pure water-producing system is usually fed to a pure water-containing tank 1. The pure water which is once stored in the pure water-containing tank 1 is fed to the ultrapure water line which comprises a circle line (conduit) 2 containing therein a series of the various treatment equipments adapted to subject the pure water to the ultimate purification to afford ultrapure water. The ultrapure water as obtained from the ultimate purification of pure water taking place in the ultrapure water line is allowed to flow out through a point 3 of use of the ultrapure water. At the point 3 of use, the ultra-pure water is thus drawn from the ultrapure water line and distributed to the actual sites of use of ultrapure water, for instance, the sites of production of semi-conductors. The volume of the ultrapure water which has not been drawn out at the point 3 of use and is still remaining in the line is returned to the pure water-tank 1 by way of the return section of the circle line (conduit) 2.

As shown in FIG. 1, the primary pure water is fed to the pure water tank 1 from the primary pure water-producing system. In the pure water tank 1, the space above the stored pure water is filled with nitrogen gas to protect the pure water from its possible contamination with carbon dioxide gas in the air.

Connected to the tank 1 is the circle line (conduit) 2 to which the primary pure water is fed and purified finally to ultrapure state during its circulation through the line. The primary pure water which is flowing via the line (conduit) 2 is thus subjected to the final purification by being sterilized, deionized and filtered, whereby ultrapure water is produced. The circle line 2 is equipped with a circle pump 4 for circulating the pure water, an ultraviolet-radiating sterilizer 5 for killing viable cells of microorganisms by ultraviolet rays, and an ion exchange resin unit 6 adapted to perform the ion exchange thereinside for the purpose of achieving the deionization, such as a mixed bed polisher of the cartridge-type having an inlet 6a and an outlet 6b therefor and containing therein a cation exchange resin and an anion exchange resin in mixture or in separate beds of the resins arranged within this polisher, as well as an ultrafiltration membrane unit 7 for filtering out fine solid particles from the water. The circle line 2 also includes the point 3 of use, which distributes the ultrapure water to actual sites of use of ultrapure water. At the point 3 of use, the ultrapure water is distributed from the line 2 to the actual sites of use through the distribution pipes via valves 3' when these valves are opened. Upon effecting the sterilization of the ultrapure water line, the valves 3' are closed to terminate the distribution of the ultrapure water from the line. To permit drainage of the sterilizing aqueous solution as the waste effluent right before the tank 1 by opening a drain valve 8', a drain tube 8 is branched out from the circle line 2.

Upon effecting the sterilization of the ultrapure water line, the volume of the pure water in the tank 1 is first adjusted to a suitable level and an aqueous HF solution is injected into the pure water tank. The amount of HF to be injected is adjusted in such a way that the water present in the entire circle line 2 becomes an aqueous solution containing 1-100 ppm of HF. Here, the concentrations of HF in the HF solution which are lower than 1 ppm cannot bring about sufficient sterilization effects. However, the concentrations of HF in the HF solution which are higher than 100 ppm are insignificant because they cannot bring about any additional meritable effects, but require a higher HF cost and result in a greater load to an ion exchange resin upon the subsequent removal of HF. Accordingly, the most suitable HF concentration may range from about 10 ppm to about 50 ppm in the method of the present invention.

Next, a conduit section 2a which positions on the upstream side of the inlet 6a of the cartridge-type mixed bed ion exchange resin polisher 6 and another conduit section 2b which positions on the downstream side of the outlet 6b of the polisher 6 (hereinafter, these conduit sections 2a and 2b are called "inlet-side conduit section" and "outlet-side conduit section", respectively, for the sake of brevity) are disconnected from the inlet 6a and outlet 6b of the polisher 6, respectively and are directly connected to each other to form and establish a bypass circuit section 2ab as shown by dotted lines in the drawing. As a result, the HF solution can pass and circulate via the bypass circuit 2ab through the line 2 while bypassing the polisher 6, namely, without flowing through the polisher 6. After forming the bypass circuit section 2ab outside the polisher 6, the circle pump 4 is started to circulate the aqueous HF solution via the bypass circuit 2ab through the ultrapure water line, namely the line 2. The sterilization effects can be enhanced further if a small amount of the aqueous HF solution is drawn at the point 3 of use by controlled operation of the valves 3'.

After the ultrapure water line 2, including the bypass circuit 2ab, has been completely filled up with the aqueous HF solution having a predetermined HF concentration, the circle pump 4 is stopped so that the aqueous HF solution is allowed to remain in the stationary state for about 1 hour within the line 2. The insides of the line 2, including the insides of the various devices equipped in the line 2, are therefore exposed to the aqueous HF solution, whereby the ultrapure water line is sterilized. After confirming that the total kill of viable cells is achieved in the ultrapure water line, the inlet-side conduit section 2a and the outlet-side conduit section 2b which are forming the connection of the bypass circuit section 2ab for bypassing the polisher 6 are disconnected from each other. The inlet-side conduit section 2a and the outlet-side conduit section 2b are then immediately connected to an inlet 10a and outlet 10b of a cartridge-type anion exchange resin polisher 10 containing a basic anion exchange resin, for example, "Duolite A-102D" or "Duolite A-378" (both, trade names), and the circle pump 4 is again started. While the aqueous HF solution is circulated again in this manner through the ultrapure water line, the fluoride anions $F^-$ are successively adsorbed on the anion exchange resin to be removed from the aqueous HF solution which has exerted the sterilization in the line 2. When the fluoride anions $F^-$ have been substantially eliminated in the above manner (for example, this can be confirmed when the electric resistivity of the water as measured by a resistivity meter CI provided at a point downstream of the ultrafiltration membrane unit 7 which is arranged in the ultrapure water line 2 has increased to a value of approximately 0.1 M$\Omega$.cm), the circle pump 4 is stopped. Thereafter, the cartridge-type anion exchange resin polisher 10 is disconnected and instead, the mixed bed ion exchange resin polisher of the cartridge-type 6, wherein a cation exchange resin and an anion exchange resin are charged as a mixture or in separate beds of the resins, is connected back again to the conduit sections 2a and 2b.

The circle pump 4 is then started to circulate the water through the line 2, in an attempt to re-start the production of ultrapure water. Then, the electric resistivity of the water inside the line 2 immediately soon increases and the quality of the water at the point 3 of use is improved in a short time to a sufficient level of purity to use it as ultrapure water. Since a highly pure HF aqueous solution as employed contains foreign ions at extremely low levels in contrast to an aqueous $H_2O_2$ or NaClO solution as conventionally employed, contamination of the ultrapure water line due to the residual foreign ions can be minimized during the operation of the method of this invention.

Incidentally, many of semiconductor-manufacturing factories have facilities for the treatment of waste aqueous effluents containing hydrofluoric acid or the like. In such factories, after the exposure of the inside of the ultrapure water line 2 to the aqueous HF solution was effected according to the sterilization method of this invention, it is possible to drain the aqueous HF solution from the pure water tank 1 via a valved drain tube 9, to replenish primary pure water to the tank 1 and then to conduct the above-described operation for increasing the electric resistivity of the water in the line 2. This makes it possible to purify the water which is existing in the line 2, ultimately into ultrapure water, with shortening further the time required until the electric resistivity of the water increases to a predetermined level. Furthermore, the load of the $F^-$ ions to the basic anion exchange resin can be reduced. The above-described operation is therefore preferred.

COMPARATIVE EXAMPLE AND EXAMPLE

In the ultrapure water line which is diagammatically shown in FIG. 1 and which was incorporated in an ultrapure water-producing system or plant and was able to feed ultrapure water at 2 m$^3$/hr to the point 3 of use of ultrapure water, the valves 3' of the distribution pipes were first closed at the point 3 of use so that the distribution and supply of ultrapure water to the actual sites of use of ultrapure water was stopped. Sterilization of the ultrapure water line was then conducted using an aqueous solution of 1 wt. % of $H_2O_2$ in accordance with the conventional method. Thus, the inlet-side conduit section 2a and the outlet-side conduit section 2b were disconnected from the cartridge-type mixed bed polisher 6 shown in FIG. 1. The thus-disconnected conduit sections 2a and 2b were directly connected to each other, thereby forming a bypass circuit 2ab which bypassed the polisher 6. The primary pure water tank 1 was then charged with an electronics-grade 35% aqueous $H_2O_2$ solution of such a volume that the ultrapure water line 2 could be fed and filled up with an aqueous solution of 1 wt. % $H_2O_2$. The circle pump 4 was then started and 30 minutes later, the circle pump 4 was stopped. The aqueous $H_2O_2$ solution as fed was then allowed to remain for 60 minutes in the line 2, including the bypass circuit 2ab, whereby the insides of the line 2 were exposed to the $H_2O_2$ solution and hence sterilized. Thereafter, the aqueous $H_2O_2$ solution which was contained in the tank 1 was completely discharged through the drain tube 9. The valve 8' was switched over so that water would be discharged through the drain line 8 at a point in the return section of the line 2, said point being located right upstream of the tank 1. Thereafter, while charging and replenishing a volume of fresh primary pure water into the primary pure water tank 1, the circle pump 4 was started to feed the primary pure water into and through the ultrapure water line. The circle pump 4 was then stopped when the $H_2O_2$ concentration of the effluent flowing out through the drain line 8 had dropped to 0.1 ppm or lower.

The inlet-side conduit section 2a and the outlet-side conduit section 2b which were connected directly to each other at the bypass connection circuit 2ab were then disconnected from each other. The thus-disconnected inlet-side conduit section 2a and the outlet-side conduit section 2b were then connected back to the inlet 6a and outlet 6b of the cartridge-type mixed bed polisher 6, and the circle pump 4 was started again to circulate water through the line 2. After confirming that the electric resistivity of water as measured at the outlet of the ultrafiltration membrane unit 7 had increased to 17.5 $M\Omega.cm$ when measured by the resistivity meter CI, the number of the viable cells present in samples of an ultrapure water as drawn from the point 3 of use was counted, and the sterilization process with $H_2O_2$ was finished.

After completion of the above sterilization process with $H_2O_2$, the ultrapure water line 2 was operated to run for 1,000 hours to conduct commercial production of ultrapure water. Thereafter, the sterilization method according to the present invention was practiced. Thus, the inlet-side conduit section 2a was disconnected from the inlet 6a of the cartridge-type mixed bed polisher 6 provided in the ultrapure water line 2 as shown in FIG. 1, and the outlet-side conduit section 2b was also disconnected from the outlet 6b of the polisher 6. The thus-disconnected conduit sections 2a and 2b were then connected directly to each other, thereby forming a bypass circuit connection 2ab to permit the bypassed feeding of water via said bypass circuit but without flowing through the cartridge-type mixed bed polisher 6. Thereafter, the primary pure water tank 1 was charged with an approximately 50% aqueous HF solution of electronics-grade (product of Morita Kagaku Kogyo Co., Ltd.) of such a volume that the ultrapure water line 2 could be filled up with an aqueous solution containing 10 ppm of HF. The pump 4 was started to circulate the aqueous HF solution through the line 2 via the bypass circuit 2ab. The circle pump 4 was then started and 30 minutes later, the circle pump 4 was stopped. The HF solution was then allowed to remain for 60 minutes in the line 2, whereby the inside of the conduits and each equipment provided in the line 2 was exposed to the HF solution and hence sterilized.

Thereafter, the inlet-side conduit section 2a and the outlet-side conduit section 2b which had been directly connected to each other at the bypass circuit 2ab were disconnected from each other. The free ends of the conduit sections 2a and 2b thus disconnected were connected respectively to an inlet 10a and outlet 10b of a cartridge-type anion exchange resin polisher 10 containing a weakly basic anion exhange resin (e.g. "Duolite A-378"), and the circle pump 4 was started. The aqueous HF solution was circulated through the line 2 via the polisher 10. While the aqueous HF solution was caused to flow through the bed of the anion exchange resin of the polisher 10, the $F^-$ ions were removed.

Here, the flow rate of the water through the line 2 was lowered to 0.7 $m^3/hr$ from a usual rate of 2 $m^3/hr$ in order to facilitate the elimination of the $F^-$ ions by the weakly basic anion exchange resin. When the electric resistivity of the water as measured at the outlet of the ultrafiltration membrane unit 7 had increased to at least 0.1 $M\Omega.cm$ and thus substantial removal of $F^-$ ions was confirmed, the pump 4 was stopped. From the inlet 10a and outlet 10b of the cartridge-type anion exchange resin polisher 10, the respective conduit sections 2a, 2b were then disconnected. The conduit sections 2a, 2b were connected back to the inlet 6a and outlet 6b of the cartridge-type mixed bed polisher 6 which was originally positioned. The pump 4 was started again to circulate the water through the line 2. When the resistivity of the water as measured at the outlet of the ultrafiltration membrane unit 7 had increased to 17.5 $M\Omega.cm$, indicating the attained production of ultrapure water, samples of an ultrapure water were drawn at the point 3 of use and the number of viable cells in the samples was counted.

Table 1 below shows the counts of viable cells in the ultrapure water samples as drawn from the point 3 of use of the ultrapure water line and also the overall volumes of the effluent discharged through the drain line 8, respectively, after the sterilization with an aqueous solution of 1 wt. % of $H_2O_2$ was performed by the conventional method and after the sterilization with an aqueous solution of 10 ppm of HF was performed by the present invention. Besides, the times required for the respective sterilization processes are shown in Table 1.

As is understood from the foregoing Comparative Example of the conventional method with $H_2O_2$, as well as the Example of this invention, the sterilization method of this invention can remarkably reduce the overall volume of waste effluent and the time required for the sterilization process, as compared with the conventional method.

TABLE 1

|  | Viable cell counts (cells/ml) | Volume of waste effluent discharged through drain line 8 ($m^3$) | Time for sterilization work (hr) |
| --- | --- | --- | --- |
| Primary pure water supplied to the pure water tank | 80–150 | — | — |
| Sterilization with 1 wt. % of $H_2O_2$ (Comparative Example) | 0 | 5 | 6 |
| Sterilization with 10 ppm of HF | 0 | 0 | 3 |

TABLE 1-continued

| | Viable cell counts (cells/ml) | Volume of waste effluent discharged through drain line 8 (m$^3$) | Time for steri-* lization work (hr) |
|---|---|---|---|
| (Invention Example) | | | |

*The time denotes such time duration that passed from the injection of the aqueous solution of $H_2O_2$ or HF into the primary pure water tank until the sampling of ultrapure water at the point of use in the case when the sterilization process was conducted by two workers.

As has been described above, when the sterilization of an ultrapure water line with an aqueous HF solution and the subsequent removal of HF with an anion exchange resin are conducted in accordance with the present invention, there is not produced any waste effluent containing $H_2O_2$ or NaClO at a high concentration unlike the conventional method which makes use of $H_2O_2$ or NaClO. In addition, it is possible to conduct the sterilization process of an ultrapure water line in a shortened time, in contrast to the prior art method which has heretofore required a long time for satisfactory sterilization of the ultrapure water line.

Besides, the sterilization method according to the present invention does not use any oxidizing agent so that the materials of the ultrapure water line-constituting devices or units such as ion exchange resins and the materials of the various equipments provided in the ultrapure water line will not be deteriorated.

We claim:

1. A method for the sterilization of an ultrapure water line provided in an ultrapure water-producing system, which comprises passing through the ultrapure water line an aqueous solution containing hydrofluoric acid as a sole sterilizing agent at a concentration of 1-10 ppm, so that the ultrapure water line is sterilized.

2. A method for the sterilization of an ultrapure water line provided in an ultrapure water-producing system, said ultrapure water line comprising an ion exchange resin unit as well as an inlet-side conduit section and an outlet-side conduit section as connected to an inlet and an outlet of the ion exchange resin unit, which method comprises:
   (a) disconnecting from the ion exchange resin unit and connecting the inlet-side conduit section and the outlet-side conduit section directly to each other to form a bypass circuit and to permit bypassed feeding of water through said bypass circuit without passing the water through the ion exchange resin unit provided in the ultrapure water line;
   (b) passing an aqueous solution containing hydrofluoric acid at a concentration of 1-100 ppm, through the ultrapure water line which has been rearranged by the direct connection of the inlet-side conduit section to the outlet-side conduit section to form the bypass circuit and permit the bypassed feeding of said solution without passing said solution through the ion exchange resin unit, whereby the sterilization is effected in the so rearranged ultrapure water line; and
   (c) allowing the aqueous solution of hydrofluoric acid to remain within the ultrapure water line having been so rearranged to have the bypass circuit, until the sterilization has been completed in said ultrapure water line.

3. The method of claim 2, further comprising: (d) disconnecting the inlet-side conduit section and outlet-side conduit section from each other after the completed sterilization, whereby the previous direct connection of the inlet-side conduit section to the outlet-side conduit section for permitting the bypassed feeding of an aqueous solution of hydrofluoric acid without the passage through the ion exchange resin unit is thus broken;
   (e) immediately after the disconnection, connecting the inlet-side conduit section and the outlet-side conduit section respectively to an inlet and an outlet of a basic anion exchange resin unit as separately provided;
   (f) circulating the aqueous hydrofluoric acid solution, which has been used for the sterilization of the line, through the basic anion exchange resin unit and through the ultrapure water line, to remove the fluoride ions from the aqueous hydrofluoric acid solution by the basic anion exchange resin; and
   (g) continuing the step (f) of circulation of the aqueous hydrofluoric acid solution until the remaining fluoride ions are removed from the circulating aqueous solution and the circulating aqueous solution becomes substantially free of the fluoride ions, but without discharging any fluoride ion-containing aqueous solution as an effluent from the ultrapure water-producing system.

4. The method of claim 3, further comprising:
   (h) replacing the basic anion exchange resin unit by a cartridge-type mixed bed ion exchange resin unit subsequently to the completion of the step (g) where the fluoride ion-containing aqueous solution has been continued to be circulated for the removal of fluoride ions by the basic anion exchange resin unit, with the cartridge-type mixed bed ion exchange resin unit as replaced being connected to said inlet-side conduit section and said outlet-side conduit section, respectively, and being thus incorporated in the ultrapure water line;
   (i) circulating further the water remaining in the ultrapure water line, through the cartridge-type mixed bed ion exchange resin unit and through the ultrapure water line so that further removal of any residual ions and other impurities present in the water is achieved by the cartridge-type mixed bed ion exchange resin unit; and
   (j) continuing the circulation of the water through the cartridge-type mixed bed ion exchange resin unit and through the ultrapure water line until the electric resistivity of the circulating water reaches 17.5 M$\Omega$.cm when measured at an outlet side of an ultrafiltration unit provided in the ultrapure water line and thus until the production of ultrapure water is ready for its re-starting.

5. The method of claim 2, in which the ultrapure water line further comprises a circle pump and an ultraviolet-radiating sterilizer on the upstream side of the ion exchange resin unit and comprises an ultrafiltration unit on the downstream side of the ion exchange resin unit but on the upstream side of the point of use of the ultrapure water as produced.

* * * * *

UNITED STATES PATENT AND TRADEMARK OFFICE
CERTIFICATE OF CORRECTION

PATENT NO. : 5,147,605
DATED : September 15, 1992
INVENTOR(S) : TATSUNO et al

It is certified that error appears in the above—identified patent and that said Letters Patent is hereby corrected as shown below:

Cover Page, Item [73], after "Japan" insert --Nomura Micro Science Co., Ltd., Tokyo, Japan--.

Signed and Sealed this

Third Day of May, 1994

Attest:

BRUCE LEHMAN

Attesting Officer

Commissioner of Patents and Trademarks